United States Patent
Cleary et al.

(10) Patent No.: US 7,867,981 B2
(45) Date of Patent: Jan. 11, 2011

(54) COMPOSITIONS COMPRISING HIGHLY PURIFIED AMPHOTERICIN B

(75) Inventors: John D. Cleary, Brandon, MS (US); Stanley W. Chapman, Jackson, MS (US); Robert E. Kramer, Brandon, MS (US)

(73) Assignee: University of Mississippi, University, MS (US)

( * ) Notice: Subject to any disclaimer, the term of this patent is extended or adjusted under 35 U.S.C. 154(b) by 0 days.

(21) Appl. No.: 10/529,622

(22) PCT Filed: Oct. 3, 2003

(86) PCT No.: PCT/US03/31390

§ 371 (c)(1),
(2), (4) Date: Mar. 30, 2005

(87) PCT Pub. No.: WO2004/030677

PCT Pub. Date: Apr. 15, 2004

(65) Prior Publication Data

US 2006/0105968 A1    May 18, 2006

Related U.S. Application Data

(60) Provisional application No. 60/415,671, filed on Oct. 3, 2002.

(51) Int. Cl.
*A61K 31/70*    (2006.01)

(52) U.S. Cl. .......................................... 514/31; 536/6.5
(58) Field of Classification Search .................... 514/31
See application file for complete search history.

(56) References Cited

U.S. PATENT DOCUMENTS

| | | | |
|---|---|---|---|
| 3,965,090 A | 6/1976 | Metzger | |
| 4,035,568 A | 7/1977 | Schaffner et al. | |
| 4,049,898 A | 9/1977 | Metzger | |
| 4,054,734 A | 10/1977 | Metzger | |
| 4,308,375 A * | 12/1981 | Tang | 536/6.5 |
| 4,656,288 A * | 4/1987 | Ono et al. | 548/244 |
| 4,663,167 A | 5/1987 | Lopez-Berestein et al. | |
| 4,766,046 A | 8/1988 | Abra et al. | |
| 4,902,789 A * | 2/1990 | Michel et al. | 536/6.5 |
| 5,194,266 A | 3/1993 | Abra et al. | |
| 5,616,334 A | 4/1997 | Janoff et al. | |
| 5,965,156 A | 10/1999 | Proffitt et al. | |
| 6,406,713 B1 | 6/2002 | Janoff et al. | |

\* cited by examiner

*Primary Examiner*—Elli Peselev
(74) *Attorney, Agent, or Firm*—Stites & Harbison PLLC; Richard S. Myers, Jr.

(57) ABSTRACT

A method for treating fungal infections in a mammal that includes administering a therapeutically effective amount of a composition comprising substantially pure amphotericin B and a pharmaceutically acceptable carrier. Amphotericin BHP is associated with decreased toxicity in mammals and cells measured by cell viability and expression of cytokine markers. Thus, this method allows for reduced adverse reactions when using amphotericin B products.

17 Claims, 3 Drawing Sheets

FIGURE 1. HPLC FRACTIONS

FIGURE III

CYTOKINE RESPONSE INDUCED BY AMPHOTERICIN BHP

COMPOSITIONS COMPRISING HIGHLY PURIFIED AMPHOTERICIN B

PRIORITY

This application claims priority to U.S. Patent Application No. 60/415,671, filed on Oct. 3, 2002, the contents of which are incorporated herein by reference.

FIELD OF THE INVENTION

The present invention relates to the field of highly purified amphotericin B (amphotericin BHP) compounds, compositions, and methods of use thereof. More specifically, the present invention relates to the treatment of fungal infections in mammals.

The purification techniques of the present invention allow for the isolation of polyene anti-fungals from the supernatant of *Streptomyces nodosus* cultures.

BACKGROUND OF THE INVENTION

Amphotericin B products are used to treat a variety of fungal infections, including systemic fungal infections.

However, amphotericin B induces serious adverse reactions. This background will describe the amphotericin B adverse reactions, discovery of a mechanism for the adverse reactions, and a description of markers of these reactions.

Amphotericin B is used primarily an intravenous agent in the treatment of severe fungal infections. However, its usefulness is compromised by a high incidence of adverse effects [flu-like symptoms (fever, chills, myalgias), capillary leak syndrome (hypotension, decreased organ perfusion), pulmonary congestion, changes in mental status (lethargy, confusion, agitation), renal dysfunction with secondary hypokalemia, hypomagnesemia and anemia, and liver dysfunction]. These adverse reactions are observed in up to seventy percent of treated patients. The mechanisms responsible for these reactions are, to date, not entirely known.

Through molecular biologic techniques, the present inventors have discovered inflammatory cytokine genes that are up-regulated (increased in cells) after exposure to amphotericin B. The genes include interleukin-1, a potent inflammatory cytokine. The adverse effects associated with stimulation of interleukin-1 are discussed below.

Proposed mechanisms of amphotericin B induced "flu like syndrome" include the expression of interleukin-1 (IL-1), tumor necrosis factor (TNF) or prostaglandins by mononuclear cells which then alter the hypothalamic set point inducing fever and chills. Administration of endotoxin causes similar reactions. Amphotericin B-exposed mononuclear cells induces unique morphological changes and dramatically altered protein expression. Some host cell proteins have been reported to be inducible by amphotericin B, such as TNF-α and IL-1β. The present inventors have demonstrated that this protein expression is not associated with release of preformed protein; protein release is associated with up-regulation of a gene or derepression of an inhibitory gene.

Currently, pharmacologic agents used to prevent amphotericin B adverse reactions only address small aspects of the problem. Hydrocortisone is used to prevent the flu-like syndrome and hypotension. Acetaminophen is also used to prevent the flu-like syndrome. Fluids administered parenterally are used to prevent renal dysfunction. Also, lipid products have been developed to decrease the toxicity of amphotericin B. These products encapsule or protect amphotericin B from causing these reactions. However, they are not totally successful.

What is needed, then, is an amphotericin B product and treatment method without the high incidence of side effects.

SUMMARY OF THE INVENTION

The invention is the discovery of an improved method of isolation for amphotericin B achieved through purification, called amphotericin BHP. Amphotericin BHP is associated with decreased toxicity in mammals and cells measured by cell viability and expression of cytokine markers. Thus, the present invention allows for reduced adverse reactions when using amphotericin B products. In certain embodiments of the present invention, amphotericin BHP is obtained from high pressure liquid chromatography fractionation.

One embodiment of the present invention is a pharmaceutical composition comprising substantially pure amphotericin B. For the purposes of this invention, substantially pure is greater than about 90% pure. Preferably, substantially pure amphotericin is greater than about 96% pure. In other embodiments, the amphotericin B is greater than about 97, 98, or 99% pure.

Another embodiment of the present invention is a method of treating fungal infections in a mammal, comprising administering a therapeutically effective amount of the highly purified amphotericin B compound of the present invention and a pharmaceutically acceptable carrier to a mammal in need thereof.

Another embodiment of the present invention is a method of testing toxicity in patients treated with pharmacological agents. This embodiment includes a method of testing patients treated with amphotericin B.

Another embodiment of the present invention is a pharmaceutical composition comprising an amphotericin B formulation, wherein the amphotericin B formulation comprises no greater than about 4% by weight of impurities.

These and other embodiments will become clear from a reading of the disclosure and claims.

DETAILED DESCRIPTION OF THE INVENTION

As indicated above, while amphotericin B has been recognized as a valuable material, particularly in its powerful antifungal properties, its clinical (i.e. therapeutic use) has been limited because of the severe side effects to the subject being treated. Amphotericin B is insoluble in aqueous solution, consequently it is supplied commercially as a combination of Amphotericin B, lipid carriers, desoxycholate and/or buffers, suspended in a glucose solution to form a colloidal suspension for administration to the patient. It is usually given intravenously over a period of from two to six hours. Faster infusions may result in cardiotoxicity. Other toxic effects of Amphotericin B may manifest themselves as renal disfunction, anemia, fever and hypotension.

The toxicity of Amphotericin B limits the total amount of the drug which may be used in the treatment of a fungal infection. Furthermore, it is often ineffective in neutropenic and immunodeficient patients, patients who are highly susceptible to fungal infections. Consequently, there is a need for a system which decreases the toxicity of Amphotericin B to the mammalian system while simultaneously enhancing its effectiveness against the fungal infection.

It has recently been shown that the encapsulation of certain drugs in lipid carriers before administration to the patient can markedly alter the pharmacokinetics, tissue distribution, metabolism and therapeutic efficacy of these compounds. Further, the distribution and pharmacokinetics of these drugs can be modified by altering the lipid composition, size, charge and membrane fluidity of the lipid carriers in which they are encapsulated.

The highly purified amphotericin B composition or complex of the present invention may be formed into pharmaceutical compositions, and may be administered in accordance with known procedures of administering amphotericin B products to a subject.

For example, the highly purified amphotericin B composition if the present invention may be formed into a lipid formation. Conventional amphotericin B may be complexed with a lipid component that enables solubility in aqueous solutions, thus allowing for parenteral administration. Over the past two decades, researchers have investigated the utility of incorporating amphotericin B into phospholipid vesicles (liposomes) and/or cholesterol esters in order to provide larger amounts of parent drug and concomitantly, less nephrotoxicity. To date, at least three lipid formulations of amphotericin B are commercially available: amphotericin B lipid complex (ABLC, Abelcet); amphotericin B cholesteryl sulfate complex, also called amphotericin B colloidal dispersion (ABCD, Amphotec); and liposomal amphotericin B (L-AmB, AmBisome). The present invention may be used in connection with each commercially available formulation, and one of ordinary skill in the art would understand how to substitute the highly purified amphotericin B of the present invention for the commercially available amphotericin used in the commercial formulation.

The current United States Food and Drug Administration (FDA) approved dosages for the three lipid formulations are believed to be as follows: L-AmB, 3-5 mg/kg/day; ABLC, 5 mg/kg/day; and ABCD, 3-4 mg/kg/day. The lipid formulations can safely be administered at daily dosages 5 to 10 fold higher than the daily dosages of amphotericin B.

The following chart identifies commercially available amphotericin B drugs that may incorporate the highly purified amphotericin product of the present invention:

TABLE 1

Examples of Commercially Available Amphotericin B Drugs

| Generic Name | Trade Name | Manufacturer/ Marketer | FDA |
| --- | --- | --- | --- |
| Amphotericin B deoxycholate (AmBD) | Amphotericin B | (generic) | 1958 |
| Amphotericin B lipid complex (ABLC) | ABELCET ™ | The Liposome Company | 1995 |
| Amphotericin B cholesteryl sulfate complex, amphotericin B colliodal dispersion (ABCD) | AMPHOTEC ™ | SEQUIS Pharmaceuticals | 1996 |
| Liposomal amphotericin B (L-AmB) | AMBISOME ™ | Fujisawa USA and NeXstar Pharmaceuticals | 1997 |

The chemical properties and physical characteristics of available amphotericin B products are outlined in the Table 2, below:

TABLE 2

Chemical and Physical Properties of Examples of Amphotericin B Drugs

| | Lipid Configuration | Size (Nanometers) | Lipid Component | Amphotericin B content (mol %) |
| --- | --- | --- | --- | --- |
| AmBD | Micelle | <25 | soduim deoxycholate | — |
| ABLC | Ribbon-Like | 500–5000 | dimyristoylphosphatidylcholine dimyristoylphosphatidylglycerol | about 33% |
| ABCD | Disc-Like | 125 | cholesteryl sulfate | about 50% |
| L-AmB | Unilamellar vesicle (spherical) | 90 | hydrogenated phosphatidylcholine cholesterol distearoylphospohatidlglycerol | about 10% |

The amphotericin BHP compositions of the present invention may be administered to a patient in an amount ranging from about 0.001 milligrams per kilogram of body weight per day to about 1000 mg per kg per day, including all intermediate dosages therebetween. It will be readily understood that "intermediate dosages", in these contexts, means any dosages between the quoted ranges, such as about 0.001, 0.002, 0.003, etc.; 0.01, 0.02, 0.03, etc.; 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, etc.; 3, 4, 5, 6, 7, 8, 9, 10, etc.; 12, 13, 14, etc.; 50, 51, 52, 53, 54, etc.; 100, 101, 102, 103, 104, etc.; 500, 501, 502, 503, etc.; 600, 700, 800, 900, and about 1000 mg per kg per day, and including all fractional dosages therebetween.

In other embodiments, the amphotericin BHP compositions of the present invention may be administered to a patient in an amount ranging from about 0.01 milligrams per kilogram of body weight per day to about 100 mg per kg per day, including all intermediate dosages therebetween.

In yet other embodiments of the present invention, the amphotericin BHP compositions of the present invention may be administered to a patient in an amount ranging from about 0.1 milligrams per kilogram of body weight per day to about 10 mg per kg per day, including all intermediate dosages therebetween.

The pharmaceutical compositions of the present invention may be administered by any known route, including parenterally and otherwise. This includes oral, nasal (via nasal spray or nasal inhaler), buccal, rectal, vaginal or topical administration. Administration may also be by orthotopic, intradermal subcutaneous, intramuscular, intraperitoneal or intravenous injection and/or infusion. Such compositions may be administered as pharmaceutically acceptable compositions that include pharmacologically acceptable carriers, buffers or other excipients. The phrase "pharmacologically acceptable" refers to molecular entities and compositions that do not produce an adverse, allergic or other untoward reaction when administered to a human. For treatment of conditions of the lungs, the preferred route is aerosol delivery to the lung via bronchoalveolar lavage or the like.

Of course, with respect to conventional amphotericin intravenous injection and/or infusion appears to be the most popular delivery route. In such embodiments, the amphotericin BHP compositions of the present invention may be administered gradually over a period of time ranging from 0.001 h to 100 h. In other embodiments, when administration of the pharmaceutical compositions of the present invention via intravenous injection and/or infusion is the preferred route, the pharmaceutical compositions of the present invention should administered gradually over a period of time ranging from 0.1 h to 50 h. In other embodiments, when administration of the pharmaceutical compositions of the present invention via intravenous injection and/or infusion is the preferred route, the pharmaceutical compositions of the present invention should administered gradually over a period of time ranging from 1 h to 10 h.

As stated above, the highly purified amphotericin B of the present invention may be part of an HDLC (high drug:lipid ratio complexes). As one example of this embodiment, the amphotericin BHP composition of the present invention may be used in the same manner as the amphotericin B complex disclosed in in U.S. Pat. No. 6,406,713, incorporated herein by reference. Those embodiments include HDLC systems which comprise lipids and bioactive agents including drugs. Such HDLCs may comprise phospholipids such as DMPC and DMPG, preferably in a 7:3 mole ratio or saturated phospholipids or fatty acid phospholipids. The bioactive agent for these embodiments is the highly purified amphotericin B of the present invention. Examples of the mole percent of the highly purified amphotericin B includes examples where the amount is from about 6 to about 70 mole percent. Other example are in the about 30 to about 50 mole percent. Pharmaceutical compositions of the HDLCs of the present invention may be made comprising pharmaceutical acceptable carriers or diluents, and these compositions may be administered parenterally. Of course, such compositions are used to treat infectious diseases such as fungal infections, by administering them to mammals such as humans. The HDLC-containing compositions of the present invention include those compositions substantially free of liposomes and compositions substantially free of liposomes entrapping the drug. The term "substantially free" in this context shall be taken to mean generally no more than about 10 percent by weight of liposomes, no more than about 5%, and/or no more than about 3%.

Various methods for preparing the HDLCs of these embodiments are disclosed in the U.S. '713 patent, including, for example, techniques that first solubilize the highly purified amphotericin B in a solvent such as DMSO or methanol. In an alternative method, lipid particles (or liposomes) containing highly purified amphotericin B containing about 6 percent to 50 mole percent amphotericin B are formed and then the particles (or liposomes) are subjected to a heating cycle, at about 25° C. to about 60° C. Such a cycle forms a more highly ordered and less toxic amphotericin B/lipid complex.

As further examples, the amphotericin BHP of the present invention may be used in the manner and amounts described in U.S. Pat. Nos. 3,965,090; 4,663,167; 4,766,046; 4,054,734; 5,965,156; 4,049,898; 5,194,266; and 4,035,568, all of which are incorporated herein by reference.

The mode of administration of a preparation of the present invention may determine the sites and cells in the organism to which the amphotericin BHP compound will be delivered. Generally speaking, the highly purified amphotericin composition of the present invention will be administered in admixture with a pharmaceutical carrier selected with regard to the intended route of administration and standard pharmaceutical practice. For instance, delivery to a specific site may be most easily accomplished by topical application (if the infection is external, e.g., on areas such as eyes, skin, in ears, or on afflictions such as wounds or burns). Such topical applications may be in the form of creams, ointments, gels, emulsions, or pastes, for direct application to the afflicted area. Alternatively, the preparations may be injected parenterally, for example, intravenously, intramuscularly, or subcutaneously. For parenteral administration, they can be used, for example, in the form of a sterile aqueous solution which may contain other solutes, for example, enough salts or glucose to make the solution isotonic. Other uses, depending on the particular properties of the preparation, may be envisioned by those skilled in the art.

For therapeutic administration to humans, the prescribing physician will ultimately determine the appropriate dosage for a given human subject, and this can be expected to vary according to the age, weight, and response of the individual as well as the nature and severity of the patient's symptoms. in the curative or prophylactic treatment of fungal or viral diseases, The dosage of the drug in the HDLC or liposomal form will generally be about that employed for the free drug. In some cases, however, it may be necessary to administer dosages outside these limits. The prescribed amount may vary when used for curative and prophylactic treatment of fungal or other infectious diseases.

The following examples are submitted to show embodiments of the present invention. They are intended to show embodiments of the present invention and be exemplary of aspects of the present invention and not intended to be limiting thereof.

The examples illustrate other embodiments of the present invention and are designed as an in vitro evaluation of amphotericin B components fractionable through high pressure liquid chromatography using the described methods.

EXAMPLE 1

Reagents

Aliquots of about 11.2 mg of powder are measured from commercial grade amphotericin B manufacturers. In this example, Amphotericin B manufactured by Apothecon and Sigma are utilized. These aliquots contain about 5 mg of amphotericin B. Each sample is stored at about 4° C. in microcentrifuge tubes and diluted immediately prior to each experiment. The 5 ug/mL dilution is made by adding about 1.0 mL sterile water to each aliquot. The 2.5 ug/mL is made by using about a 2:1 dilution of about 500 uL of the 5 ug/mL stock. The Sigma brand is not a pharmaceutical grade product and is selected as a positive control representing a "minimally purified" product. Fresh aliquots are diluted prior to each experiment and agitated immediately before use. A sample aliquot from each amphotericin B preparation is reserved for testing endotoxin contamination.

Other pharmacologic agents utilized include *Escherichia coli* endotoxin (Serotype 026:b6 lipopolysaccharide, Sigma; St. Louis, Mo.) (LPS), desoxycholate and sodium phosphate buffer which are obtained from Sigma. These reactions are used as positive and negative controls for IL-1β expression from mononuclear cells. Reagents used in the IL-11βexpression assay are diluted with sterile water so that 0.01 ml of stock solutions added to culture wells resulted in the final concentrations noted.

EXAMPLE 2

Mononuclear Cell Preparation

Unsupplemented media (RPMI-1640) is obtained from Flow Laboratories (McLean, Va.). Mononuclear cells [THP-1; ATCC 222:U937] is resuspended to a final concentration of approximately $5\times10^6$ cells/mL in supplemented media (RPMI-1640, about 10% autologous serum, about 100 ug/mL streptomycin and about 100 u/mL penicillin). About one milliliter of mononuclear cells is seeded in Limbro 24-well plates (Flow Laboratories; McLean, Va.) and incubated for 24 hours at 37° C. in 5% $CO_2$.

EXAMPLE 3

Assays

High Pressure Liquid Chromatography Isolation and Validation: Amphotericin B aliqotes of Example 1 are applied to a 4.6×150 mm 5 micron AquaC18™ column (Phenomenex®), and components resolved isocratically using about 70% methanol:about 30% 5 mM sodium citrate (pH 7.0) (vol:vol) flowing at a rate of about 1 ml per minute. Column eluant is monitored at about 305 nm and about 405 nm. Specific composition of the solvent varies from about 70:30 (methanol:sodium citrate) to about 75:25 (methanol:sodium citrate) to achieve the best resolution of high purity amphotericin B and other components.

Viability Assay: Amphotericin B fractions are tested for effects of human cell viability. A tritriated thymidine incorporation assay in addtion to Erythrocin red or Trypan Blue are exclusion dye tests is used. Assays of cytotoxic activity using tritriated thymidine are performed under aerobic conditions. Substances to be assayed are diluted in RPMI containing about 10% human or bovine serum, added to the first vertical column of a 96-well flat-bottom tissue culture plate, and serially diluted in RPMI in the remaining wells of each row using a multi-tip pipetter. Control rows without drugs or containing solubilizing agents (DMSO, DOC, glycerin) are similarly treated so that the concentrations of these diluents are similarly decreased across the plate. Logarithmic growth phase THP-1 cells are added (about $10^6$ cell per well), and the plates maintained in a $CO_2$ incubator (about 5% $CO_2$ in air; about 37° C.) for about 24 hours. At the end of this drug-exposure phase, the plates are centrifuged about 5 min at about 200×g, the supernatants are briskly decanted, and the wells refilled with PBS. After the third such rinse, the wells are refilled with drug-free RPMI. The plates are returned to the $CO_2$ incubator, and any remaining viable cells allowed to grow during a 24-hour amplification phase. The plates are then centrifugally washed twice with PBS, and the wells refilled with RPMI-1640 (Sigma) containing about 10% FBS and about 5 mCi/well [methyl-$^3$H] thymidine (New England Nuclear, Boston, Mass.) and incubated for about an additional hour. The plates are then harvested to glass-fiber paper using distilled water rinses, and the paper counted with a $Matrix_{96}$ gas-ionization direct-beta counter (Packard Instrument Co, Meriden Conn.). Each drug exposure is done in triplicate rows of a single plate. Each plate included controls for the cytotoxicity of solubilizing agents (DMSO, DOC, glycerin) and a drug-free control. Radioactivity per well is analyzed with Microsoft-Excel. The assay differentiates target cell death from drug-induced loss of motility since it measured incorporation of radioactivity into newly synthesized DNA after drug washout. Minimum lethal concentration (MLC) is defined as the lowest concentration of drug (in a 1:2 serial dilution series) to kill all the target cells (reduce incorporation to background levels). The 100% control level (no killing) for each plate is defined as the mean radioactivity per well of the drug-free control row. Experimental results are expressed as percent of the control mean using the drug-free control as 100%. This assay is adapted for use with mammalian cells in tissue culture monolayers by substituting DME containing 10% FBS for the RPMI and by extending the tritiated thymidine pulse labeling period in RPMI/10% FBS to an overnight incubation.

In vitro Infusion Related Reaction Assay: Amphotericin B is added to Limbro 24-well plates at final concentrations of about 0 ug/mL and 20 ug/mL. Cells are then incubated for about 2 hours. Supernatants are collected from each well after three freeze-thaws and stored at about −70° C. until assay. Samples are assayed for IL-1β using an enzyme-linked immunosorbent assay (Cistron Biotechnology; Pine Brook, N.J.) (ELISA). The procedure involves a four-step test carried out in microtiter wells which are coated with IL-1β specific monoclonal antibody. Manufacturer's data indicate an assay sensitivity of 20.0 pg/mL and a specificity for IL-1β. There is no cross-reactivity for IL-1α, IL-2, TNF-α or interferon. Evaluations of assay precision demonstrate a coefficient of variation of about 5.3% to about 6.7% for intra-assay variability and about 6.6% to about 8.4% inter-assay variability. Data are the mean of duplicate assays and are expressed in pg/mL on the basis of standards supplied by the manufacturer.

Amphotericin B Assay: A polyclonal rabbit antibody is isolated from New Zealand white rabbits after standard immunization with amphotericin B complexed with an immune adjuvant, Keyhole Limpet Hemocyanin. An anti-amphotericin B antibody is purified by filtering serum through an Aminolink Affinity-Pak Column (ImmunoPure Ag/Ab; Pierce Chemical Co., Rockford, Ill.), diluted to a final concentration of 180 ug/mL and frozen at about −70° C. until further use. The ELISA is initiated by removing a light protection cover from an amphotericin B-bovine serum albumin coated microtiter plate. The 1.0 ug/mL coating solution is emptied, and triplicate well washings are performed. Wash solution consisted of a standard phosphate buffered salt solution containing tween. The 96-well plates are then blocked with bovine serum albumin for one hour at about 37° C. and again thrice washed. Addition of amphotericin solution (100 ul) is followed by Anti-amphotericin B antibody (100 ul) and then incubation for about an hour at about 37° C. Plates are emptied and thrice washed. Horseradish peroxidase-anti-rabbit IgG diluted 1:1000 in buffer is added after blot drying. Plates are again incubated for an additional hour at about 37° C. and thrice washed. A 200 uL aliquot of peroxidase substrate solution [Fast-P-9187; Sigma Chemical, St. Louis, Mo.] is pipetted into each well and ELISA plates are tested after about 10 minutes for photometric density [Dynatech multiscan; Flow Laboratories, McLean, Va.] utilizing a 405 nm filter. Finally, amphotericin B-spiked samples are tested for stability during storage at about −70° C. for about 60 days. Triplicate light-protected samples at amphotericin B concentrations of 2.5 ug/mL and 5 ug/mL are assayed by ELISA.

Published data indicate an assay sensitivity of 0.15 ug/mL. There is cross-reactivity for agents with polyene structures, nystatin and hamycin. Evaluations of assay precision demonstrates a coefficient of variation of 3.0% for intra-assay variability. Data are the mean of duplicate assays and are expressed in ug/mL on the basis of Apothecon brand as the standard.

Spectrophotometric Assay: Classification and quantification of a polyene can be performed based on each agent's ultraviolet absorption. The ultraviolet spectra for tetraenes (nystatin, amphotericin A) has characteristic peaks at about 290 nm, about 305 mu and about 318 mu, while heptaenes (amphotericin B) occurs at about 360 nm, about 378 nm and about 405 nm. The principles of Beer's Law are used to estimate the relative amount of amphotericin A or B in each preparation. Nystatin is used in our assays for amphotericin A and tested at an optical density of about 290 nm. Amphotericin B formulated by Apothecon is tested at an optical density of about 360 nm. These optical densities are selected owing to their uniqueness to amphotericin A and B, respectively. Peaks at other optical densities are shared with pentaenes and hexaenes, making it difficult to preclude their existence in the solution. Two unique peaks for pentaenes are identified at optical densities of about 325 nm and about 333 nm. Samples of each amphotericin formulation are diluted in about 1.0 mL DMSO, then further diluted with about 5 mL methanol. A 400 uL aliquot from this dilution is further diluted in about 5 mL of methanol. A dilution of sodium desoxycholate does not affect the optical density measurements. Ultraviolet light absorbance from about 200 nm to about 450 nm is determined with a Gilford Spectrophotometer and analyzed by Response II software (Gilford; Dayton, Ohio). Data are the mean of triplicate assays, and amphotericin concentrations are expressed in micrograms per milliliter on the basis of Apothecon brand as the standard for amphotericin B and nystatin as the standard for amphotericin A.

EXAMPLE 4

Susceptibility Testing

Antifungal Agents: Stock solutions of sample agents are prepared by dissolving stock powder in dimethyl sulfoxide (DSMO) and appropriately diluted using RPMI 1640 buffered to about pH 7.0 with about 0.165M morpholinepropanesulfonic acid (MOPS) (PML Microbiologicals, Wilsonville, Oreg.). The final concentration of DMSO is such that the concentration in test solutions comprised less than about 6% of the total solution composition.

Test Isolates: One *Candida albicans* isolate, American Type Culture Collection (ATCC) strain 90028, is selected.

DMSO inhibitory test: Effects of DMSO on MIC determination are tested using NCCLS broth microdilution guidelines and the test isolate *C. albicans* 90028. One hundred microliters of a DMSO and an RPMI solution are placed in the wells of a microdilution tray so that the concentrations of DMSO in tested wells are 1, 2, 3, 4, 5, 6, 7, 8, 9, 10, 15, 20, 25, and 30 percent. Yeast inoculum is prepared as described in antifungal susceptibility testing, and 100 gl are added to each test well. The trays are incubated in a humid, dark chamber for about 48 hours at about 35° C. The MIC is determined as any visible change in growth when compared to control. DMSO inhibitory tests are preformed in duplicate.

Antifungal Susceptibility Testing: Sample MIC's are determined by broth microdilution according to NCCLS guidelines. Isolates are subcultured twice on potato dextrose agar (PDA) plates (Remei, Lenexa, Kans., USA). Fungal suspensions are prepared by transferring four to five colonies into about 5 mL of sterile about 0.9% saline. The suspensions are standardized, using spectrophotometric methods, and diluted in RPMI 1640 buffered to about pH 7.0 with 0.165M MOPS (PML Microbiologicals, Wilsonville, Oreg.) to yield an initial inoculum of $0.5 \times 10^3$-$2.5 \times 10^3$ CFU/mL. 100 uL of inoculum is added to each well of a microtitre tray containing 100 uL of serially diluted drug in RPMI solution. Sample concentrations of about 0.0039, about 0.0078, about 0.0156, about 0.0312, about 0.0624, about 0.125, about 0.25, about 0.5, about 1, about 2, and about 4 ug/mL are achieved. The trays are incubated in a humid, dark chamber for about 48 hours at about 35° C. The MICs sre recorded as the wells with 80% inhibition and 100% inhibition when compared to control. MIC determinations are performed a minimum of two times with an additional run if the quantity of sample drug allowed for it. It is decided to determine the MFC on samples which achieved definitive MICs. After the MIC is read at 48-h, a 1 uL sample is withdrawn from each microtiter tray with a 96 pin replicator (Boekel, Feasterville, Pa.) and plated onto an RPMI agar plate. Samples are incubated in a humid, dark chamber for about 48 hours at about 35° C. MFC is determined by the complete lack of organism growth on the plate and recorded as the corresponding well in the MIC tray.

EXAMPLE 5

Statistical Analysis

An ANOVA is performed comparing Apothecon brand amphotericin B formulation with Sigma brand amphotericin B. A standard T-test is used to compare the differences identified within the ANOVA. An alpha of about 0.05 and a beta of about 0.2 are selected for this comparison. Sigma Stat [Jandel; San Dimas, Calif.] is utilized for the statistical analysis.

EXAMPLE 6

Results

Figure 1:
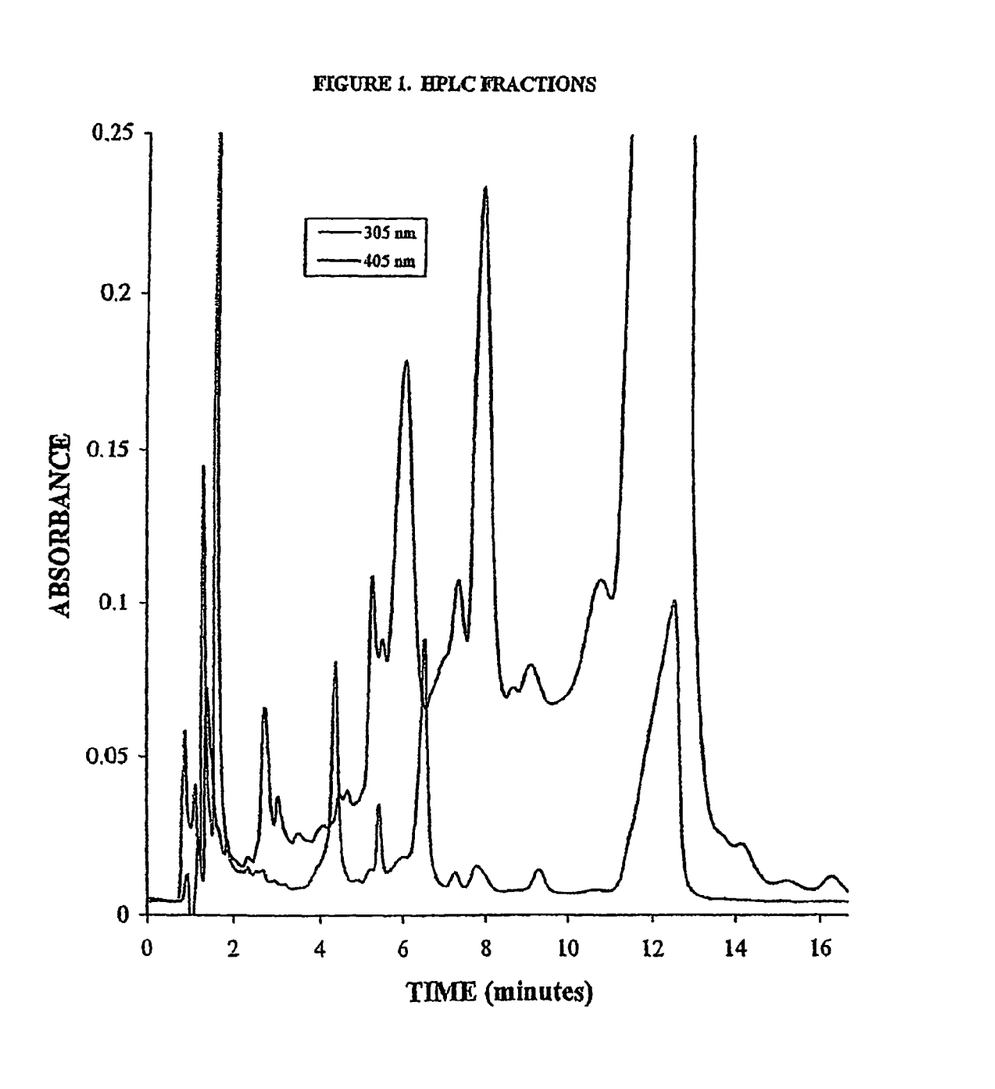
FIG. 1 is a graph that shows HPLC fractions.

High pressure liquid chromatography of amphotericin B commerically manufactured leads to the identification of multiple amphotericin products and probably bacterial/fungal endotoxin (Figure I). Isolation of each peak at optical densities of about 305 nm and about 405 nm has led to the identification of these products as polyene compounds or endotoxin. The fractions are isolated from aliquotes from commercial brand amphotericin B or Sigma brand amphotericin B resolves with using about 70% methanol:30% 5 mM sodium citrate (pH 7.0) (vol:vol) at a flow rate of about 1 mL/minute. The fraction elutes from the column at about 12 minutes from a 4.6×150 mm 5 micron AquaC18™ column monitored at about 305 nM and about 405 nM. This component is highly purified amphotericin B (Amphotericin BHP).

Viability Assay

Figure 2:
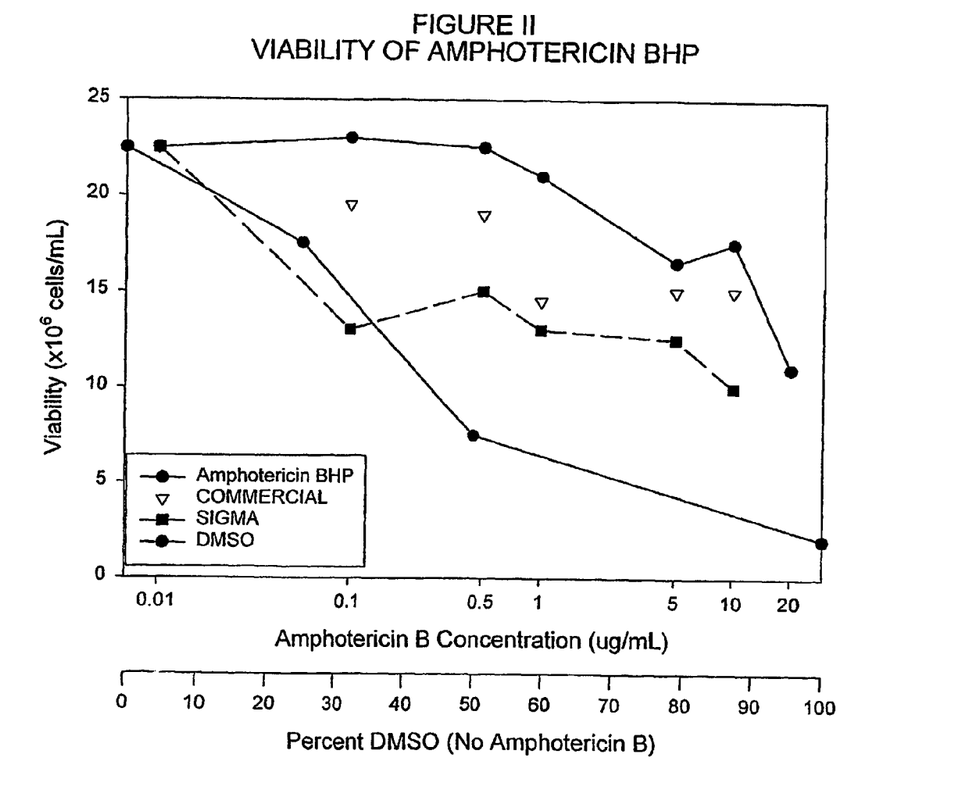
FIG. 2 is a graph that shows viability of amphotericin B compositions of the present invention versus commercial formulations.

Viability of cells is directly related to the quantity of DMSO used to solubilize amphotericin BHP. Therefore, only concentrations less than about 6% are utilized. In addition, deoxycholate solution is used to solubilize amphotericin BHP. Doxycholate did not cause decreases in viability compared to control at amounts less than about 20.2 mg per about 50 mg amphotericin B. The viability of THP-1 cells exposed to amphotericin BHP at concentrations ≦5 ug/in L is greater than the viability in cells exposed to the same contrations of commercial brand or Sigma brand amphotericin B (Figure II).

In vitro Infusion Related Reaction Assay

Figure 3:
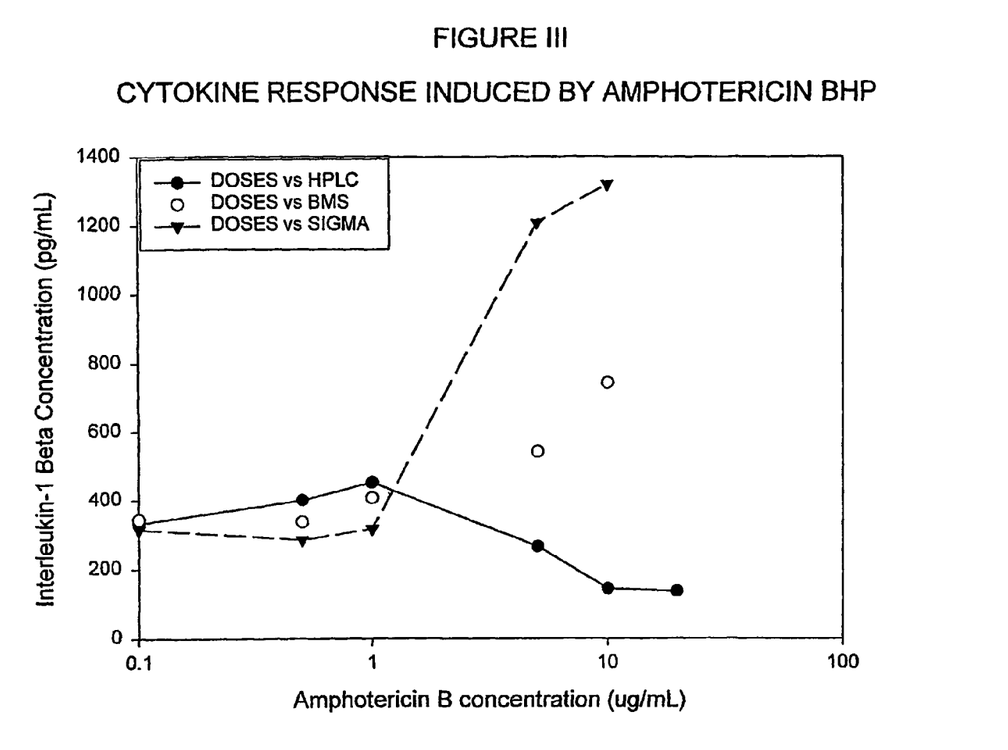
FIG. 3 is a graph that shows cytokine response induced by amphotericin B compositions of the present invention versus commercial formulations.

The potential of each of the amphotericin B formulations to induce infusion-related reactions measured by IL-1β expression are displayed in Figure III. The amount of IL-1β expression associated with THP-1 cells exposed to the individual amphotericin B formulations has been standardized to the Apothecon formulation and is represented as percent expression. Control cells exposed to sterile water or lipid express no more than about 120 pg/mL of IL-1β while Apothecon brand amphotericin B cause the expression of about 300 pg/mL and 750 pg/mL IL-1β for the 0.1 ug/mL and 10.0 ug/mL concentrations, respectively. Less cytokine is expressed in response to amphotericin BHP compared to the other formulations (Apothecon and Sigma) The difference is signficiant compared to Apothecon brand amphotericin B.

Amphotericin B Assay

Quantification of amphotericin B in stock vials is completed within about 12 hours of the IL-1β. Apothecon brand amphotericin B is measurable within about 5% of the reported values by the manufacturer. One concentration (5 ug/mL) of Sigma brand is measured at about 39.5±21.05 ug/mL. In addition, Sigma brand amphotericin B is determined to be greater than about 5% of the manufacturers labeling in all samples tested. These data, suggest that there are several polyene antifungals in Sigma brand amphotericin B which are identified by our Amphotericin B ELISA and that have spectrophotometric patterns distinct from amphotericin B.

Spectrophotometric Assay

Quantitification of amphotericin A, B, and BHP is completed by spectrophotometry. Nystatin is used as the tetraene control representing amphotericin A and Apothecon brand as the standard for the hepatene amphotericin B. The value obtained by utilizing Beer's Law (USP equation) to calculate amphotericin A should represent the amount of amphotericin A relative to the Apothecon brand. No significant differences in A or B could be found in any of the amphotericin B formulations utilized clinically (data not shown). Sigma brand amphotericin B did contain significantly more of the amphotericin A compound in comparison to the commercial brands. Based on these spectrophoto-metric results, one could hypothesize that the Amphotericin B ELISA actually effectively measures polyene antifungals as a class. However, the presence of amphotericin A is not the complete explanation for the amphotericin measured in the ELISA. There are positive correlations between both amphotericin B concentration and the concentrations of amphotericin A ($r^2=0.8831$; $p<0.01$) or interleukin-1β concentration ($r^2=0.9633$; $p<0.01$). Amphotericin BHP demonstrated a pattern consistent with polyene antifungals.

Spectrophotometric evaluations of the unique absorption maximum for each of these polyenes, except for the hexaenes, are performed. The hexaenes share all spectrophotometric peaks with either a pentaene or a heptaene. Using Beers' Law, we calculated the amount of each polyene relative to Apothecon's product. Pentaene (unique O.D. peak=333) quantities are highest in the Sigma brand (about 167%) relative to Apothecon. Heptaene (unique O.D. peak=405) content is negligible (about <6.7%) in all except the Sigma Brand (about 10.8%). There are distinct peaks at optical densities of 345, 363 and 386 that correspond to either a pentaene or a hexaene. At these peaks (345, 363 and 386), differences in the products could be easily visualized (Figure III). The peak obtained at about 12 minutes is a polyene antifungal. The peaks that occur at other time points are also polyenes.

Bacterial endotoxin contamination could explain an increased observation of infusion related reactions when switching between products. Amphotericin B manufactured by Lyphomed Pharmaceuticals in the early 1990s is identified as possibly contaminated. Therefore, we are diligent in testing our reagents for endotoxin contamination. Samples from diluent (sterile water), media, reagents and culture plates are assayed for endotoxin by the manufacturer utilizing the limulus amebocyte lysate. The limulus amebocyte lysate (LAL: Associates of Cape Cod Inc.; Woodshole, Mass.) testing employed an *Escherichia coli* endotoxin standard with a lower limit of detection of 3.0 pg/ml. Amphotericin B interferes with the LAL assay by disrupting the clot formation and clot adhesion, rendering this test difficult to perform and interpret. At concentrations achievable during clinical use, amphotericin B interference appears to be minimal. Testing of the Sigma brand and the Apothecon brand of amphotericin B preparations at 2.5 ug/mL and 5 ug/mL found no endotoxin.

Susceptibility Testing

DMSO inhibitory test. The results of the DMSO inhibitory tests displayed complete inhibition of growth at about 8% DMSO and partial inhibition at about 7%. The well with about 6% DMSO showed no visible difference from control. Therefore about 6% is set as the maximum allowable amount of DMSO in any well. Whenever possible lower concentrations are used, but due to the limited sample sizes, levels near about 6% are often used in the well with the highest drug concentration.

Antifungal Susceptibility Testing. Antifungal agents are prepared just prior to testing in all cases except in that of sample #1. After the addition of DMSO, it appeared that the drug had not completely solubilized. It is allowed to sit in the dark at room temperature for about 48 hours. The predetermined amount of RPMI is then added to the tube. An apparent exothermic reaction took place, releasing heat, and the remaining pellet dissolved completely. The sample is then used normally in susceptibility testing.

Other limitations are caused by the relatively small size of the sample drugs. Samples 2-7 are performed in duplicate and samples 1,8-12 are performed in triplicate. These low concentrations also made it impossible to test the full range of drug concentrations for each sample. Samples 3 and 6 are only tested as high as 1 ug/ml. and samples 2,5, and 7 are tested up to about 2 ug/ml. Finally, as previously discussed, the sample size required higher concentrations of DMSO than normally utilized.

TABLE 3

Activity of HPLC fractions against *Candida albicans*[1]

| ELUTION TIME | Median $MIC_{80}$ | Median $MIC_{100}$ | $MFC^{1,2}$ |
|---|---|---|---|
| 1 | >4 | >4 | NT |
| 2 | 2 | >2 | NT |
| 3 | >1 | >1 | NT |
| 4 | >4 | >4 | NT |
| 5 | >2 | >2 | NT |
| 6 | >1 | >1 | NT |
| 7 | >2 | >2 | NT |
| 8 | 1.00 | 2 | 2 |

TABLE 3-continued

Activity of HPLC fractions against *Candida albicans*[1]

| ELUTION TIME | Median $MIC_{80}$ | Median $MIC_{100}$ | $MFC^{1,2}$ |
|---|---|---|---|
| 9 | 1.00 | 2 | 1 |
| 10 | 0.25 | 2 | 0.5 |
| 11 | 0.25 | 0.5 | 0.5 |
| 12 | 0.5 | 2 | 2 |
| Solvent | NA | NA % | NA |
| AmB | 0.10 | 0.25 | 0.625 |

[1]tested against *Candida albicans* B311
[2]tested against *Candida albicans* ATCC 90028 (NCCLS-recommended strain)
MIC = Concentration (μg/ml) that inhibits 80% growth
MFC = Concentration (μg/ml) that is fungicidal to all cells (no growth is seen on agar plates)
NT = not tried due to inactivity
NA = not active
AmB = Amphotericin B High Purity
Time = elapsed time in minutes.
MIC DATA RESPRESENT THE AVERAGE OF THREE TESTS Median susceptibility results are shown in Table 3. Results with a ">" sign signify that no inhibition is observed at or below these tested levels. Sample #2 displays a "2" for $MIC_{80}$ meaning that an 80% reduction is observed in this well. Though not indicated in the table, sample #2 causes some reduction at 2 ug/mL.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Unless specifically otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

Throughout this application, various publications are referenced. All such references are incorporated herein by reference.

We claim:

1. A method for treating fungal infections in a mammal, comprising:
   providing a composition that comprises an active ingredient that includes Amphotericin B, wherein the Amphotericin B compound is present in an amount greater than 96% with no greater than 4% of impurity products, and a pharmaceutically effective carrier; and
   administering a therapeutically effective amount of said composition to a subject in need thereof.

2. The method of claim 1, wherein the amphotericin B is present in an amount greater than about 98% and no greater than about 2% of impurity products.

3. The method of claim 1, wherein said pharmaceutically acceptable carrier is a lipid carrier.

4. The method of claim 1, wherein the administering step is intravenous.

5. A pharmaceutical composition, comprising:
   an active ingredient that has at least 96% of an amphotericin B compound and no greater than 4% of impurity products, and a pharmaceutically acceptable carrier.

6. The composition of claim 5, wherein the amphotericin B compound is present in an amount greater than about 98%.

7. The method of claim 1, wherein the impurities comprise at least one of a non-amphotericin B polyene compound or an endotoxin compound.

8. The composition of claim 5, wherein the impurities comprise at least one of a non-amphotericin B polyene compound or an endotoxin compound.

9. A pharmaceutical composition that comprises:
   an active ingredient that is at least 96% w/w of a compound of the following formula:

and a pharmaceutically acceptable carrier.

10. The composition of claim 9, wherein said pharmaceutically acceptable carrier is a lipid carrier.

11. The composition of claim 9, the active ingredient comprising no greater than 4% w/w of at least one of a non-amphotericin B polyene compound or an endotoxin compound.

12. A method for treating fungal infections in a mammal, comprising:
  providing a composition that comprises an active ingredient that has at least 96% amphotericin B polyene compound and a pharmaceutically effective carrier; and
  administering a therapeutically effective amount of said composition to a subject in need thereof.

13. The method of claim 12, wherein the active ingredient that is at least 96% w/w of a compound of the following formula:

and a pharmaceutically acceptable carrier.

14. The method of claim 12, wherein said pharmaceutically acceptable carrier is a lipid carrier.

15. A pharmaceutical composition that comprises:
  an active ingredient that is at least 96% w/w of a compound of the following formula:

comprising no greater than 4% w/w of at least one of a non-amphotericin B polyene compound or an endotoxin compound,
  and a pharmaceutically acceptable carrier.

16. The composition of claim 15, wherein said pharmaceutically acceptable carrier is a lipid carrier.

17. The composition of claim 15, wherein
  the active ingredient is at least 98% w/w of a compound of the following formula:

and comprises no greater than 2% w/w of at least one of a non-amphotericin B polyene compound or an endotoxin compound; and and a pharmaceutically acceptable carrier.

* * * * *